United States Patent [19]
Riek et al.

[11] Patent Number: 5,685,820
[45] Date of Patent: Nov. 11, 1997

[54] INSTRUMENT FOR THE PENETRATION OF BODY TISSUE

[75] Inventors: Siegfried Riek, Rottweil; Karl-Heinz Bachmann; Thomas Gaiselmann, both of Villingendorf, all of Germany

[73] Assignee: Partomed Medizintechnik GmbH, Villingendorf, Germany

[21] Appl. No.: 188,339

[22] Filed: Jan. 26, 1994

Related U.S. Application Data

[63] Continuation-in-part of Ser. No. 168,213, Dec. 17, 1993, Pat. No. 5,431,151, which is a continuation of Ser. No. 779,730, Oct. 23, 1991, Pat. No. 5,271,380.

[30] Foreign Application Priority Data

Oct. 23, 1991 [DE] Germany .......................... 40 35 146.7

[51] Int. Cl.$^6$ ........................................................ A61B 1/04
[52] U.S. Cl. .......................... 600/114; 600/104; 606/185; 604/164; 604/264
[58] Field of Search .................... 604/164, 165, 604/166, 167, 264, 272; 606/185, 167; 128/4, 3

[56] References Cited

U.S. PATENT DOCUMENTS

| | | |
|---|---|---|
| 564,581 | 11/1896 | Baker . |
| 3,224,320 | 12/1965 | Knudsen . |
| 3,357,443 | 12/1967 | Fourestier et al. . |
| 3,437,747 | 4/1969 | Sheldon . |
| 3,556,085 | 1/1971 | Takahashi . |
| 3,870,036 | 3/1975 | Fiore . |
| 3,961,621 | 6/1976 | Northeved . |
| 3,994,287 | 11/1976 | Turp et al. . |
| 4,191,191 | 3/1980 | Auburn . |
| 4,248,214 | 2/1981 | Hannah et al. . |
| 4,254,762 | 3/1981 | Yoon . |
| 4,269,192 | 5/1981 | Matsuo . |
| 4,299,230 | 11/1981 | Kubota . |

(List continued on next page.)

FOREIGN PATENT DOCUMENTS

| | | |
|---|---|---|
| 135364 | 3/1985 | European Pat. Off. ............ 606/185 |
| 0 312 787 | 9/1988 | European Pat. Off. . |
| 0 347 140 | 3/1989 | European Pat. Off. . |
| 0 369 936 | 11/1989 | European Pat. Off. . |
| 0 369 937 | 11/1989 | European Pat. Off. . |
| 1370580 | 7/1964 | France . |
| 2 218 901 | 4/1972 | Germany . |
| 25 38 758 | 10/1977 | Germany . |
| 41 33 073 | 10/1991 | Germany . |
| 41 16 648 | 5/1993 | Germany . |
| 942730 | 7/1982 | U.S.S.R. . |
| 1329769 | 8/1987 | U.S.S.R. . |
| WO94/10898 | 5/1994 | WIPO . |

OTHER PUBLICATIONS

United Sates Surgical Corporation, device exhibited Oct. 10, 1993, drawing furnished.

*Primary Examiner*—Richard J. Apley
*Assistant Examiner*—Beverly M. Flanagan
*Attorney, Agent, or Firm*—Irvin A. Lavine; Nath & Associates

[57] ABSTRACT

An instrument for penetrating body tissue has a rigid hollow shaft having at its distal end a penetrating point, which is at least partly transparent and which is conical, beveled or tapered; a hollow sleeve may surround the shaft. The instrument includes or can be associated with lighting and viewing elements. There may be provided a helical element at the penetrating point, having surfaces converging outwardly to a line. In another embodiment, the point comprises plural, flat, angularly related surfaces converging to a line, the point being at least partly transparent, as by being of opaque material having one or more openings closed by a transparent window. In a further embodiment, the point has a conical distal end and has along its side at least one and preferably two blade members which is/are at or rearwardly of the apex or distal end of the conical tip, and have surfaces converging to a linear edge coaxial with the axis of the point.

31 Claims, 9 Drawing Sheets

U.S. PATENT DOCUMENTS

| | | |
|---|---|---|
| 4,319,563 | 3/1982 | Kubota . |
| 4,331,138 | 5/1982 | Sugarman . |
| 4,356,826 | 11/1982 | Kubota . |
| 4,535,773 | 8/1985 | Yoon . |
| 4,537,593 | 8/1985 | Alchas . |
| 4,567,882 | 2/1986 | Heller . |
| 4,654,030 | 3/1987 | Moll et al. . |
| 5,066,288 | 11/1991 | Deniega et al. . |
| 5,147,376 | 9/1992 | Pianetti . |
| 5,159,920 | 11/1992 | Condon et al. . |
| 5,246,425 | 9/1993 | Hunsberger et al. . |
| 5,256,149 | 10/1993 | Banik et al. . |
| 5,271,380 | 12/1993 | Riek et al. . |
| 5,290,276 | 3/1994 | Sewell . |
| 5,334,150 | 8/1994 | Kaali ..................... 604/164 |
| 5,385,572 | 1/1995 | Nobles et al. . |
| 5,441,041 | 8/1995 | Sailer et al. ............. 600/106 |

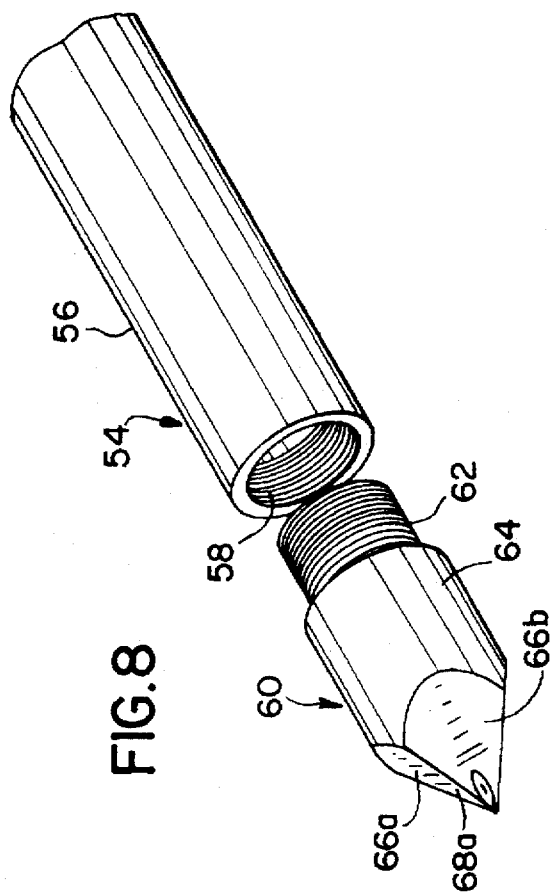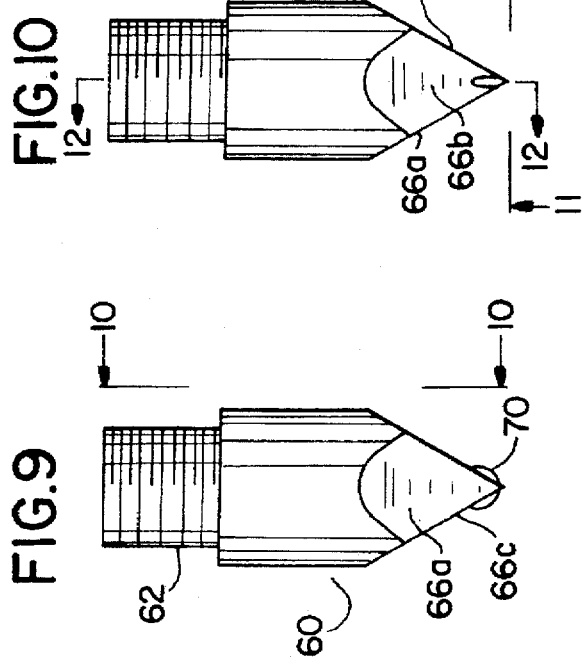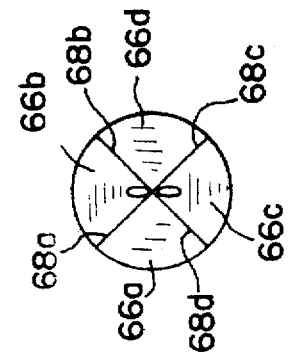

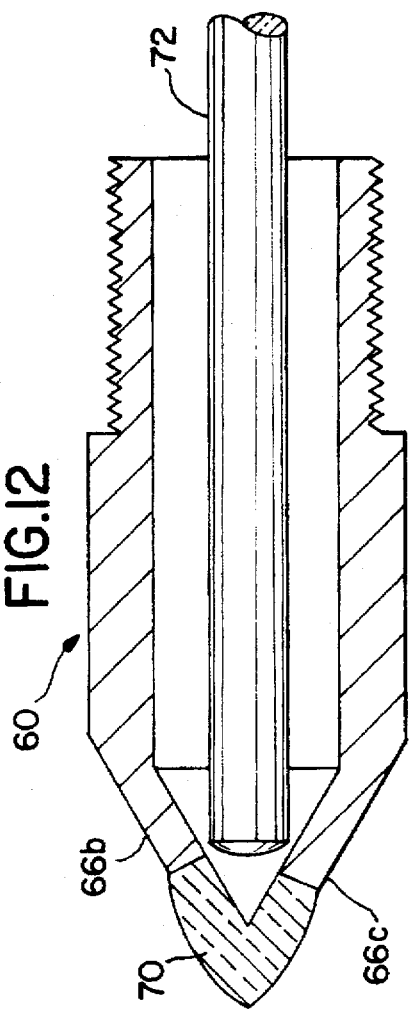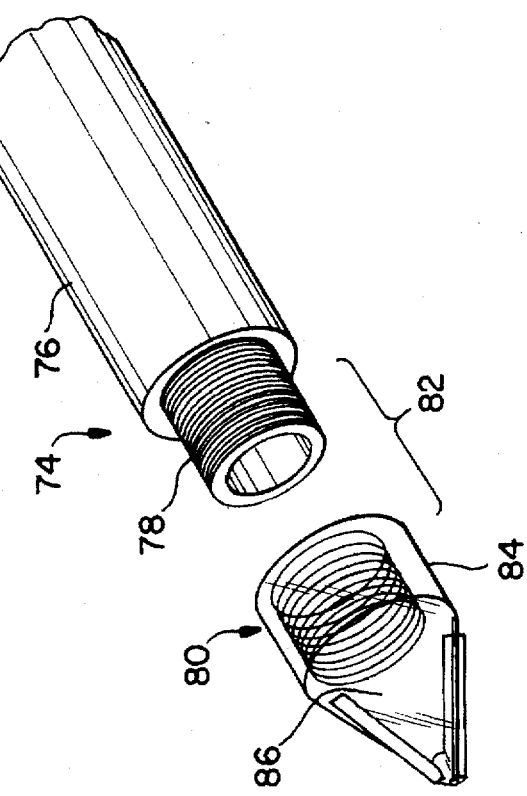

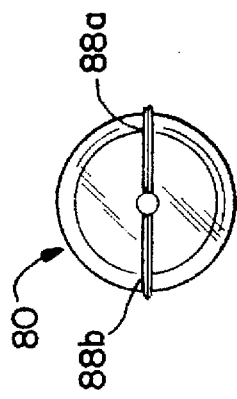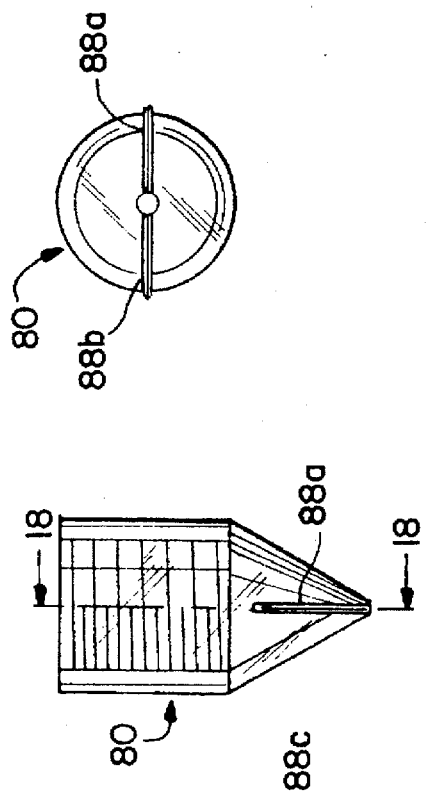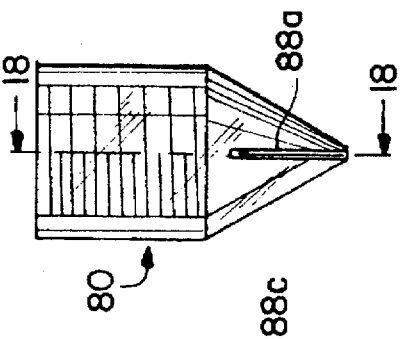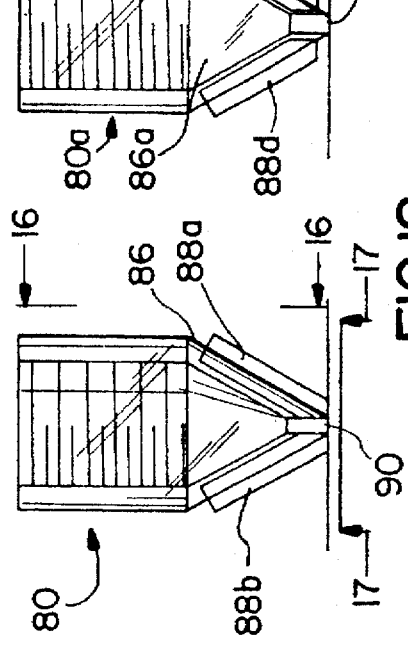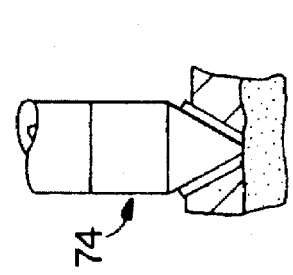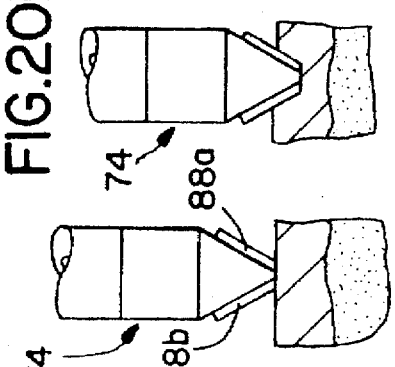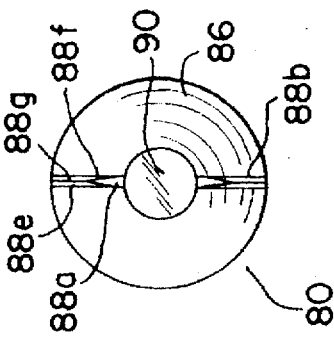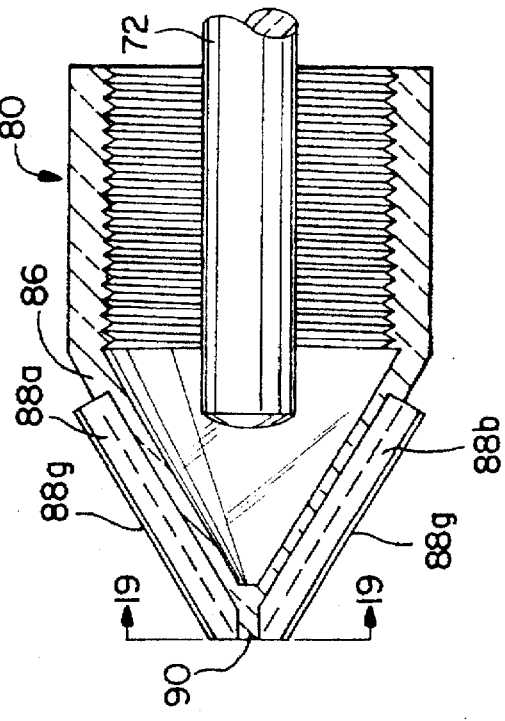

INSTRUMENT FOR THE PENETRATION OF BODY TISSUE

This application is a continuation-in-part application of application Ser. No. 08/168,213 filed Dec. 17, 1993, U.S. Pat. No. 5,431,151 issued Jul. 11, 1995 which is a continuation application of application Ser. No. 07/779,730 filed Oct. 23, 1991, U.S. Pat. No. 5,271,380 issued Dec. 21, 1993.

FIELD OF THE INVENTION

The invention relates to an instrument for the viewing and penetration of body tissue.

BACKGROUND OF THE INVENTION

Instruments of this type serve particularly as trocars to create an artificial access to body cavities or organs, which do not possess any natural communicating passage with the exterior. The instrument has a point, which serves to pierce the body tissue and to widen the perforation opening and, after removal of the trocar, represents an artificial access to the body cavity, the said access through which endoscopes, instruments, and the like can be introduced into the interior of the body.

The insertion of the trocar, even with the advantageous selection of an injection site, entails the risk of damaging blood vessels in subcutaneous fatty tissue, in fascia, and in the peritoneum ("abdominal membrane"), thus vessels in the abdominal wall. There is the further risk after penetration of the abdominal wall that the vessels in the abdominal area (abdominal cavity) and organs in the abdominal area, such as the large intestine, small intestine, omentum majus (greater omentum), and retroperitoneally located vessels and structures can be damaged. Especially at risk for damage are the small intestine and the omentum majus, if adhesions and concretions with the anterior abdominal wall are present, so that during penetration of the abdominal wall, structures adhering to the said wall may be pierced at the same time before the trocar enters the free abdominal cavity. To reduce the risk of damage, particularly to the intestine and omentum majus, a hollow needle can be passed through the abdominal wall first while the abdominal wall is lifted, to introduce gas into the abdominal cavity and to distance the abdominal wall from the underlying omentum majus and intestine for the subsequent insertion of the trocar. In that case as well, however, there is a residual risk of damage during the insertion of the hollow needle and the trocar.

DESCRIPTION OF THE RELATED ART

An instrument disclosed in DE (West German Patent) 29 22 239 C2 has an outer tube, which is beveled at the anterior distal end thereof, to form an insertion point. Two fiber-optic light bundles are run in the outer tube to the point, with the anterior end faces of the said bundles lying in the plane of the beveled face of the outer tube. The light from a light source is directed through a fiber-optic light bundle and emerges at the distal point. The second fiber-optic light bundle receives the reflected portion of this emerging light and directs the said portion to an optically sensitive element. The measured intensity of the reflected light provides information about the anatomic structure in front of the point. The alteration in the intensity of reflected light shows when the point of the instrument approaches an organ in the free abdominal cavity. During the penetration of successive tissue layers in the abdominal wall or when the point enters adhesions and concretions of organs connected to the abdominal wall, however, the reflectivity of the tissue structures in front of the point remain essentially unchanged, so that the entry of the point cannot be controlled. The beveling of the outer tube produces an insertion point, which is located near the shell of the outer tube laterally beside the emerging plane of the fiber-optic light bundles and projects beyond the said plane. The insertion point thereby limits the field of vision that can be controlled via the optic system.

A fiber-optic system functioning as a microscope is disclosed in DE-AS (Examined West German Patent Application) 16 16 107, the said system which is placed in an insertion needle. The outer tube surrounding the optic system in the needle is beveled at the distal end to form the insertion point. The tissue in front of the needle tip can be observed microscopically via the optic system. The needle cannot be employed as a trocar, because the smaller diameter thereof does not cause the widening of the perforation opening. The insertion point produced by the beveling of the outer tube produces a blind area which restricts the field of vision.

Endoscopes have been disclosed in EP (European Patent) 0 369 937 A1, EP 0 369 936 A1, and EP 0 347 140 A1, the said endoscopes which possess an outer tube wherein the fiber-optic systems are run to the point. The said endoscopes enable observation in the direction of fiber-optic fibers emerging at the point. The endoscopes are not suitable for the penetration of tissue.

A massive trocar is disclosed in DE-OS (Unexamined West German Patent Application) 22 18 901, the trocar sleeve of which possesses an outer screw thread at the proximal end thereof. The screw thread has the purpose of fixing the placed trocar sleeve more reliably against an axial displacement in the trocar-produced perforation opening.

SUMMARY OF THE INVENTION

The invention has as its object the provision of an instrument for the penetration of body tissue which reduces as much as possible the risk of damage to vessels, organs, and the like via improved optic control during insertion.

The above object is achieved with an instrument having a penetrating point, at least partly transparent, and a shaft to which the point is attached.

The novel instrument has a hollow shaft. The point or at least the distal end portion of the point is made as a window from a suitable transparent material, e.g., from glass, quartz glass, Plexiglas, or the like. An optic is run through the hollow shaft to the point, e.g., an optic with glass fiber-optic light guide, as is used in endoscopes. Furthermore, a lighting unit is run in the hollow shaft to the point. The lighting unit can be integrated into the optic in that fiber-optic fibers employed for producing illumination are placed in the tract of the optic. Likewise it is possible to run the illumination separately from the optic through the shaft to the point or also to combine lighting units integrated in the optic with additional separately introduced lighting units. The optic ends at an axial distance behind the summit of the point, so that the entire surface area of the conical window can be illuminated by the optic and observed. The operator thus has a view during the advance of the instrument of the structures to be penetrated and lying in front of the instrument point. The operator can thus recognize blood vessels, for example, before these are struck by the point of the instrument, and avoid the said vessels. In particular, the important step of the penetration of the peritoneum can proceed within view. The semitransparent peritoneum almost permits a look into the abdominal cavity before total penetration, so that the underlying omentum majus, intestines, and vascular structures in the peritoneum are discernable and damage thereto can be avoided. In addition, during the advance of the instrument, the operator can observe structures penetrated by the point and passing laterally by the surface area of the window, and thus obtains a feeling for the penetration of the point and for the rate of advance.

Because of its conical, beveled, or tapered form, the window is useful as a point, which effects both the penetration of the tissue and also the widening of the perforation opening. The special shape of the conical, beveled, or tapered window is thereby of lesser significance. Preferred is a right circular cone, because the said cone is the most simple to fabricate and produces the lowest optic distortion during observation. However, other conical, beveled, or tapered forms are also essentially possible, e.g., with a polygonal base and with a slightly crowned or slightly recessed surface line.

Because the lighting unit is placed within the point-forming window and illumination occurs through this window, it can be advantageous to derefelect the inner surface of the window. The conical, beveled, or tapered form of the window in a hollow point, however, of necessity causes an inclination of the inner window surfaces relative to the optical axis of the illumination and the optic, so that interfering reflections are minor in any event.

In an advantageous embodiment, the observation of the area lying in front of the point of the instrument can be improved still further, so that a combination of the static picture of the area lying in front of the point of the instrument with the dynamic picture of the point's advance is created for the operator. In the said embodiment, in addition to the optic viewing the entire surface area of the window, a second optic, which is formed as a thin flexible glass fiber optic, is run to the window-forming point. The said second optic is run laterally past the first optic to the window-forming point and ends at the face of the window-forming point. The said second optic with the smallest possible diameter thus provides the view of the area in front of the point, whereas the first optic enables the view of the penetrated structures adjacent to the surface area of the window. The small diameter of the second fiber optic essentially does not obstruct the observation through the first optic.

In this embodiment, the operator can observe both the advance of the instrument's point with the use of two oculars, to obtain a feeling for the path and rate of advance, and also observe the structures lying in front of the point, to avoid damage to vessels, organs, the intestine, or the omentum majus.

In all cases, the optics are formed preferably as a wide-angle optic (fish-eye optic), to offer the operator the largest possible field of vision and to enable observation through the entire surface area of the conical, beveled, or tapered window.

If the instrument is fashioned as a trocar-sleeve, then upon the insertion of the trocar with viewing, the possibility of avoiding structures at risk for damage can be employed optimally if the sleeve has an external thread. The sleeve is mounted axially stationary but rotatable on the trocar. By turning of the sleeve, the external thread thereof takes hold of the tissue and effects the advance of the trocar. The trocar with its optic does not turn in so doing. The advance via the sleeve provided with the thread enables a steady, smooth entry of the trocar point, without the operator needing to exert axial pressure on the trocar. This promotes delicate guidance of the trocar point in the area of structures at risk for damage.

To be able to turn the sleeve without great effort, the sleeve can be actuated manually via a ratchet. Actuation via an electric motor with appropriate gear reduction is equally possible.

The novel instrument disclosed is preferably employed as a trocar for the penetration of the abdominal wall and for the introduction of a trocar-sleeve into the perforation opening. Furthermore, the novel instrument disclosed can be used as a perforation needle with a thin shaft to penetrate the abdominal wall and to introduce gas into the abdominal area, so that the abdominal wall can be lifted off the internal organs before the insertion of the trocar. Finally, the novel instrument disclosed with a very fine shaft can be used in prenatal diagnosis, to pierce the amniotic sac for the removal of amniotic fluid, whereby the view through the point of the instrument safely precludes damage to the fetus.

In another embodiment of the present invention, a rotatable spiral formed of wire having surfaces converging to a helical line is on the point, and is driven by rotation of a sleeve.

In a further embodiment of the present invention, the point comprises one or more sets of surfaces which converge to a line, i.e., a linear edge which is to incise, for example, the abdominal wall, and thereby aid in penetration. The penetration point may be opaque with one or more transparent windows for permitting the passage of light and for receiving an image of tissue, etc. adjacent and in advance of the point. The converging surfaces do not extend beyond the distal end of the point, the distal end thereof being at or rearwardly of the transparent window. The converging surfaces may form the exterior surfaces of the point. In another embodiment, the point comprises a transparent hollow cone and one or more blade members are inserted in the point, having surfaces converging to a linear edge; the linear edge is coplanar with the axis of the shaft and the conical point. These members do not extend beyond the apex of the point, or in an alternate embodiment, beyond the planar truncated distal end of the point, in order that there may be viewed the tissue, abdominal wall, etc., adjacent and in advance of the instrument before the instrument is advanced, with the assistance of the linear edges, so that viewing of tissue, abdominal wall, etc. is made possible prior to penetration and the making of an incision in each part of the tissue or abdominal wall. Consequently, the surgeon is able to see tissue prior to engagement, penetration or cutting thereof.

BRIEF DESCRIPTION OF THE DRAWINGS

The invention will be described in greater detail below on the basis of embodiments presented in the figures. Shown are:

FIG. 8 is an exploded perspective view of another embodiment of an instrument for penetration of body tissue in accordance with the present invention;

FIG. 9 is an elevational view of the point shown in FIG. 8;

FIG. 10 is an elevational view taken on the line 10—10 of FIG. 9;

FIG. 11 is a view taken on the line 11—11 of FIG. 10;

FIG. 12 is a cross-sectional view taken on the line 12—12 of FIG. 10 and showing a fiberoptic bundle;

FIG. 13 is an exploded perspective view of another embodiment of an instrument for penetration of body tissue in accordance with the present invention;

FIG. 14 is an elevational view of the point shown in FIG. 13;

FIG. 15 is an elevational view of an alternate embodiment of a point;

FIG. 16 is an elevational view taken on the line 16—16 of FIG. 14;

FIG. 17 is a view taken on the line 17—17 of FIG. 14;

FIG. 18 is a cross-sectional view taken on the line 18—18 of FIG. 16, together with an optical fiber bundle;

FIG. 19 is an enlarged view taken on the line 19—19 of FIG. 18;

FIG. 20a is an elevational view of the instrument of FIG. 13 in contact with the surface of a body;

FIGS. 20b and 20c illustrate successive positions in the penetration of a body with the instrument of FIG. 13.

DESCRIPTION OF THE PREFERRED EMBODIMENTS

Figure 1:
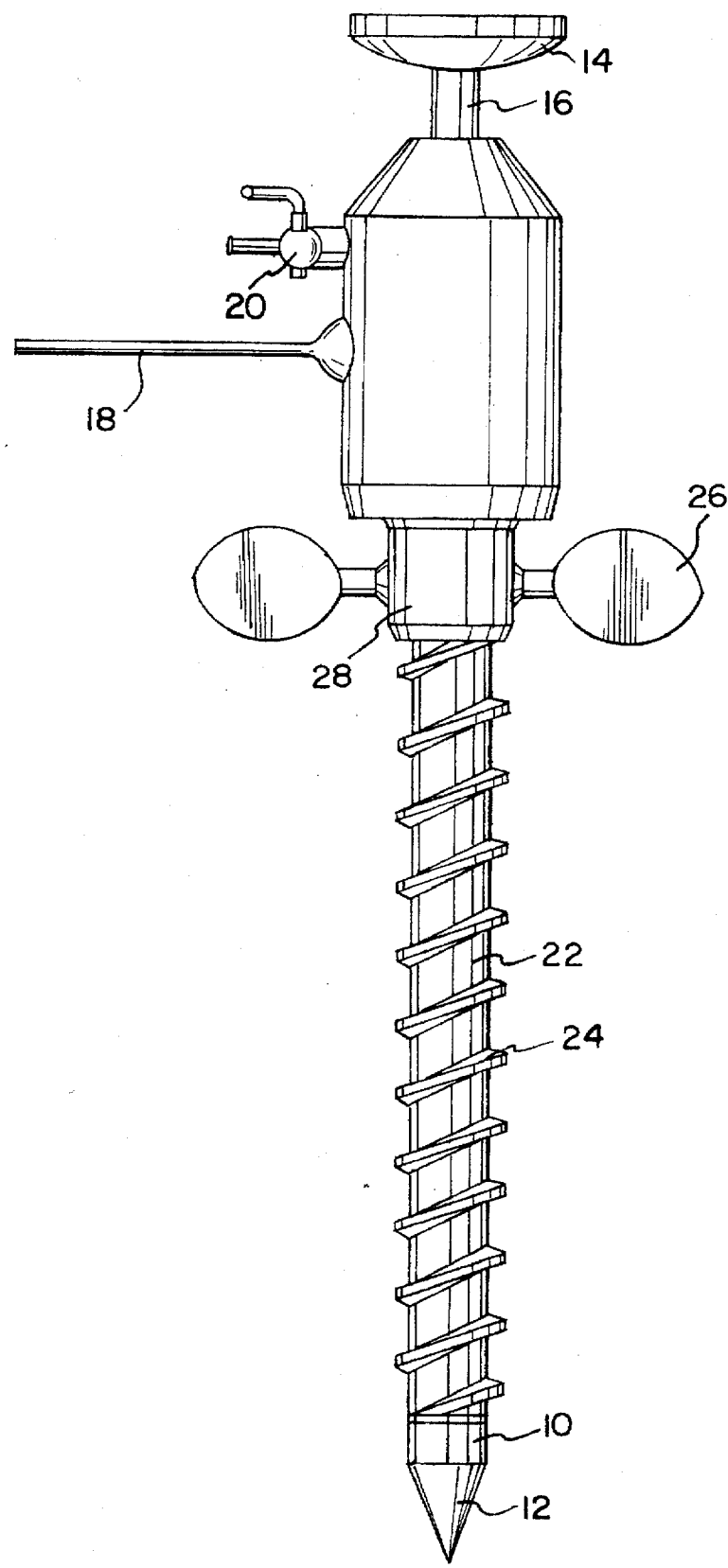
FIG. 1 is a side view of an instrument fashioned as a trocar.

The trocar shown in FIG. 1 has a hollow cylindrical shaft 10 made of steel, with a point 12, described below, inserted in the distal anterior end thereof. The eyepiece 16, provided with a cup 14, of an optic 16, placed coaxially in shaft 10 and described below, is placed at the proximal posterior end of the shaft 10. Furthermore, a fiber-optic light guide 18 of a lighting unit, described below, is introduced laterally into the posterior end of shaft 10. Finally, at the posterior end of shaft 10 an insufflation cock 20 is placed, through which for example, $CO_2$ gas can be delivered in a manner known per se to outlets, not depicted, at the anterior distal end of the shaft.

A sleeve 22 is mounted on the shaft 10 axially stationary but rotatable. The sleeve 22 has a stub thread 24 on its outer surface. The sleeve 22 can be actuated to rotate versus shaft 10 via a ratchet 28 having a toggle handle 26. An electric motor drive for the sleeve 22 is also possible. If sleeve 22 is turned on the inserted trocar, the thread 24 effects an axial advance of the trocar, whereby the said trocar itself does not turn. With the aid of the sleeve 22 provided with the thread 24, the trocar can be advanced slowly and delicately into the tissue by the operator without the exertion of axial pressure.

Figure 2:
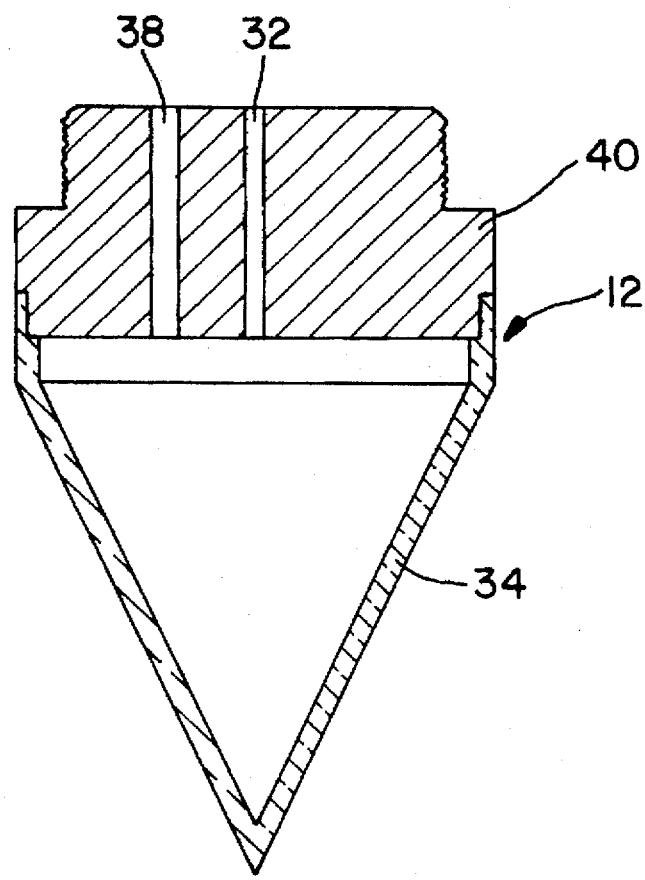
FIG. 2 is an axial section of the point of the trocar.
Figure 3:
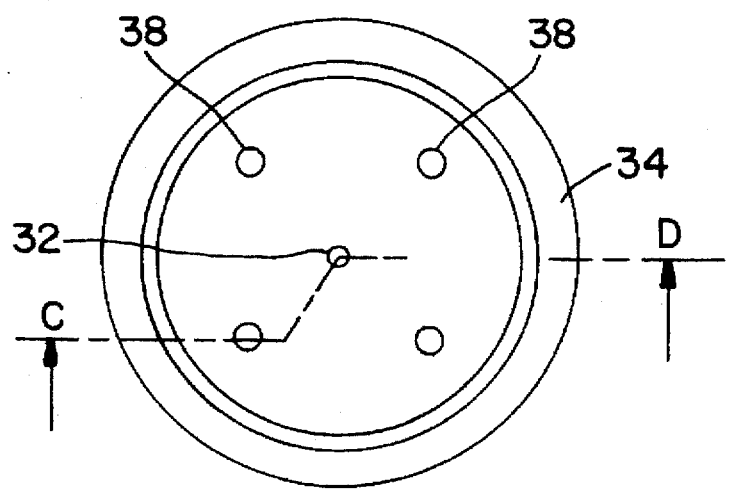
FIG. 3 is a front view of the point from the back.

As is evident from FIGS. 2 and 3, a point 12 is mounted, e.g., screwed in or soldered in, in the distal end of hollow shaft 10.

The optic 32 is inserted into an axially central drill hole leading to point 12. The optic 32 is run axially through the entire shaft 10 and ends at the proximal posterior end in eyepiece 16. The distal anterior end of optic 32 is cemented or glued in place into the drill hole of point 12.

Optic 32 is a fish-eye optic known per se, as is employed, for example, in endoscopes. A fiber-optic light guide optic is used preferentially.

Four additional drill holes, arranged equidistant around the central drill hole, are provided in point 12 parallel to the central drill hole incorporating the optic 32. A lighting unit 38 in the form of a fiber-optic light guide is inserted into the said drill holes in each case. The fiber-optic light guides of the lighting units 38 are run through the shaft 10. Light is supplied to the lighting units 38 via the fiber-optic light guide 18 and a branching.

The point 12 comprises an end flange 40 made of steel, which is mounted into the distil end of hollow shaft 10. An optic window 34 in the form of a hollow cone, bevel, or taper, made of glass, quartz glass, Plexiglas, or diamond is placed in front of end flange 40 and attached by gluing or cementing.

The end flange 40 has the central, axially passing drill hole, into which the optic 32 is inserted. Furthermore, the four drill holes, arranged around the optic, for the lighting units 38 are provided in the end flange 40. The optic 32 and lighting units 38 end at the anterior face of the end flange 40. The lighting units 38 thus illuminate the entire cone, bevel, or taper of the window 34 and optic 32 enables observation of the tissue penetrated by point 12 through the entire cone surface of window 34. The interior surface of window 34 can be dereflected if necessary.

In addition or instead of the said indirect illumination, direct illumination can also be effected, if a lighting unit, e.g., in the form of a light-conducting optic fiber, is integrated into the optic 32, the said fiber to which light is also supplied via the fiber-optic light guide 18.

The window 34 can form a sharp point, having an apex in advance of hollow shaft 10 which enables easy penetration of tissue with the trocar. Because the optic 32 does not emerge on the face of the point 12 but rather in the face, forming the base of the point 12, of the end flange 40, an optic 32 with a larger diameter can also be used, e.g., a typical rod lens system so-called Hopkins optic), which has an improved light efficiency. Here as well, the lighting unit 38 can be integrated into the optic 32. The optic 32 in this case as well is naturally a fish-eye optic.

Figure 4:
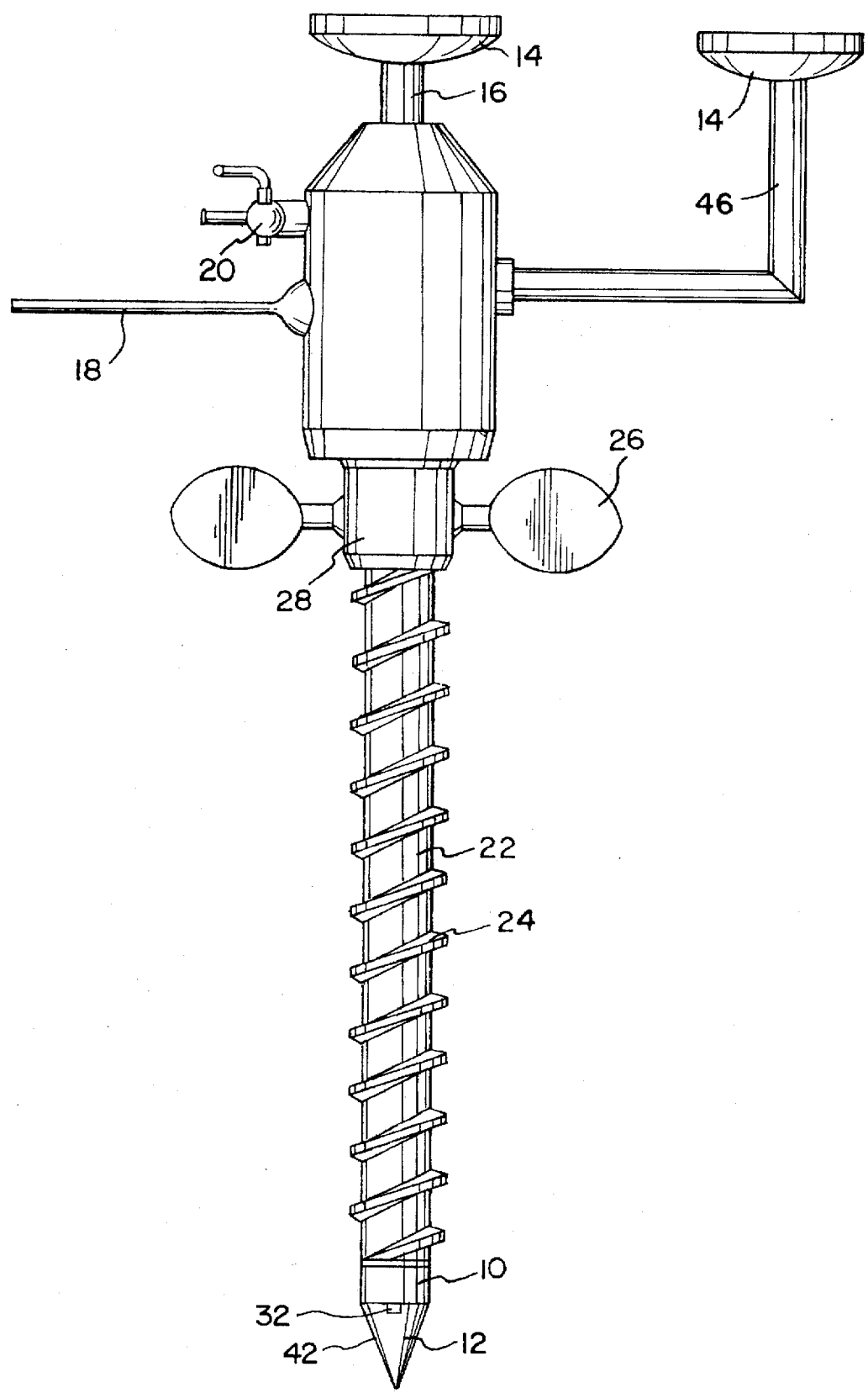
FIG. 4 is a side view of the trocar in another embodiment.
Figure 5:
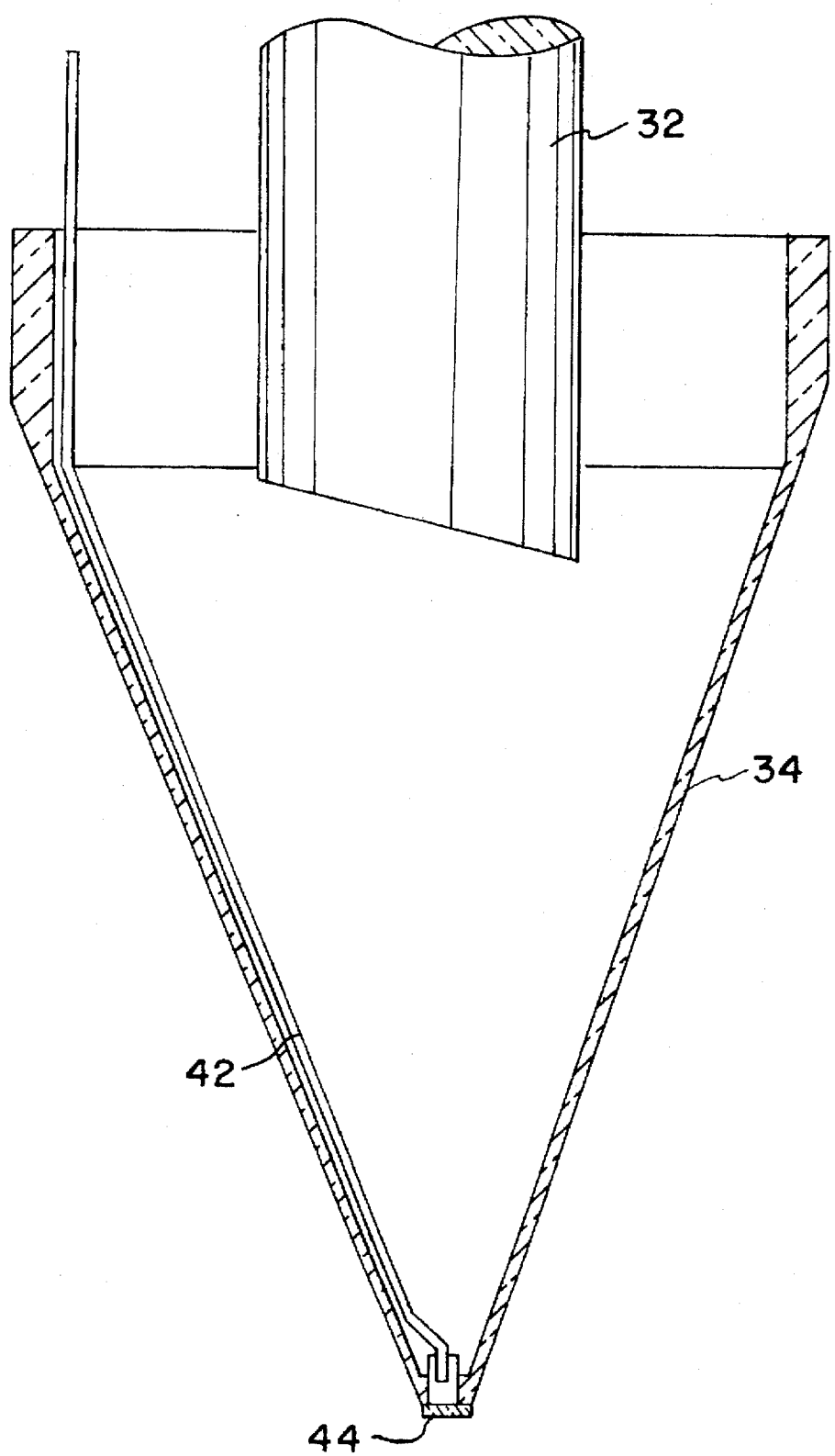
FIG. 5 is an axial section of the point of the trocar in FIG. 4.
Figure 6:
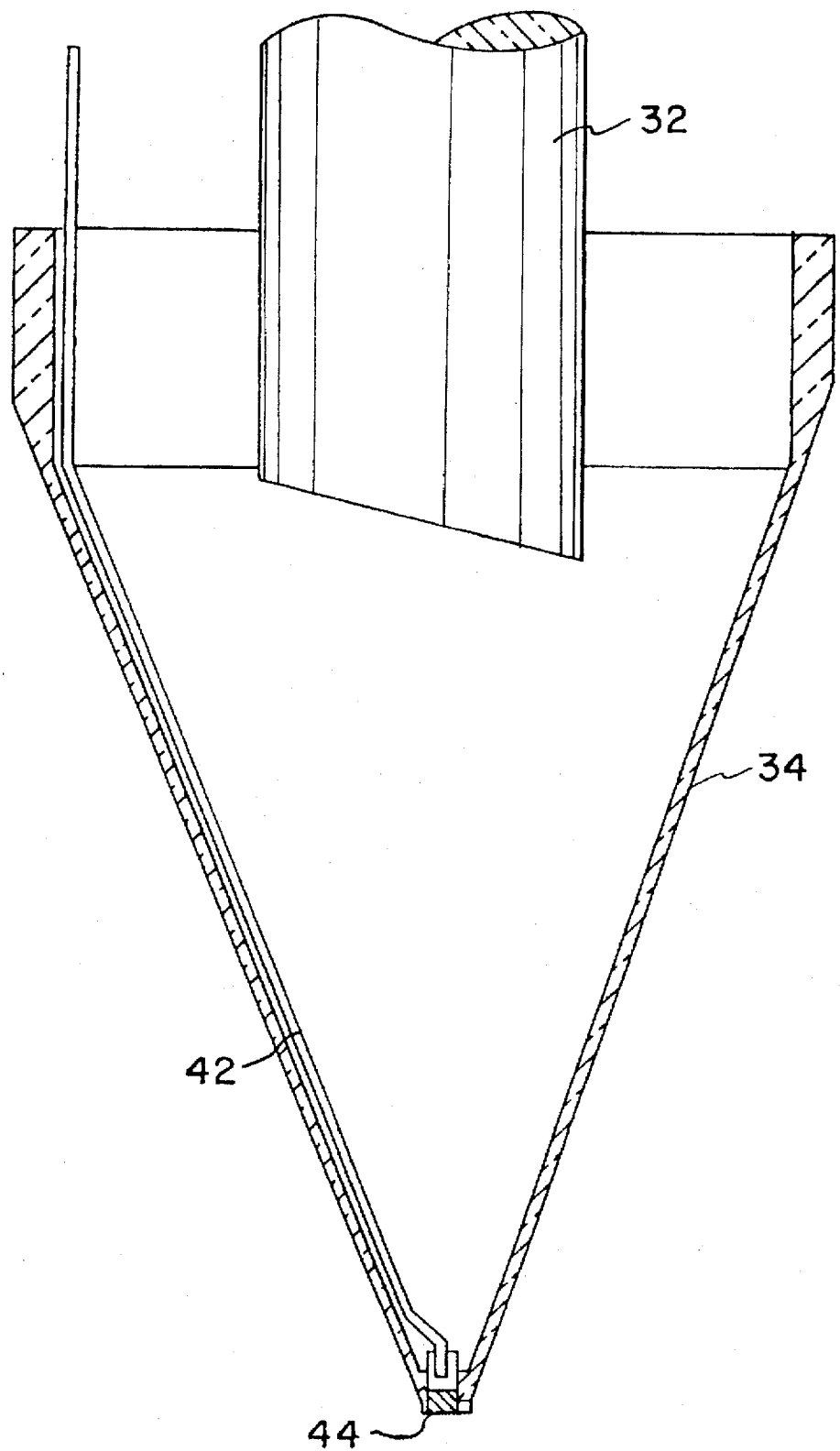
FIG. 6 is an axial section, corresponding to FIG. 5, of a modified embodiment.

Another embodiment is shown in FIGS. 4, 5, and 6.

In the said embodiment, the optic window 34 is formed as a transparent hollow cone, bevel, or taper placed on an end flange 40 of the point 12, as is described with regard to FIGS. 2 and 3. The first optic 32 is mounted axially in the center, the said optic which permits observation of the entire cone, bevel, or taper surface area of the window 34 preferably as a rod lens system.

In addition to the said first optic 32, a second optic 42 is run through the shaft 10 to the point 12. The second optic 42 is run eccentrically to the first optic 32 through the end flange 40 and proceeds interiorly along the hollow-cone window 34 to the apex of point 12. The second optic 42 emerges through the face of the conical, beveled, or tapered window 34 at the apex of the point 12. In so doing, the face can be formed by the distally most anterior part of the second optic 42. To protect the second optic 42 from pressure and soiling, a window 44 can be provided in the face in front of the second optic 42. The said window 44 can be prepared a ground surface from the material of the window 34, as is shown in FIG. 5, or can be inserted into window 34, and for example, supported axially by a collar, as is shown in FIG. 6. The second optic 42 preferably contains an integrated lighting unit. The second optic is preferably fashioned as a thin fiber-optic light guide optic with a diameter of 0.2 to 0.8 mm. Preferably, the second optic 42 is flexible, so that it can be run interiorly along window 34. The proximal posterior end of the second optic 42 is brought out laterally from shaft 10 and equipped with a second ocular 46, so that the operator can observe binocularly via both optics 32 and 42.

The second optic 42, run in the conical, beveled, or tapered window 34 to the apex of the point 12, virtually does not obstruct the view of the first optic 32, because the second optic 42 has a small diameter and preferably consists of transparent glass fibers.

The embodiment in FIGS. 4 to 6 gives the operator optimal information upon insertion of the trocar. Via the first optic 32 and the conical, beveled, or tapered window 34, he can observe the tissue structures, which have been passed through at the time, during penetration of the tissue to obtain the necessary information on the position of the point and the rate of advance. Via the second optic 42, he has a view of the tissue structures lying ahead of the point 12 immediately before the penetration thereof. The penetration of the peritoneum in particular can proceed within view, whereby the still intact semitransparent peritoneum directly before the point 12 permits a look into the abdominal cavity via the second optic to that damage to vessels in the peritoneum and the underlying omentum majus and intestines can be avoided during the penetration of the peritoneum.

Figure 7:
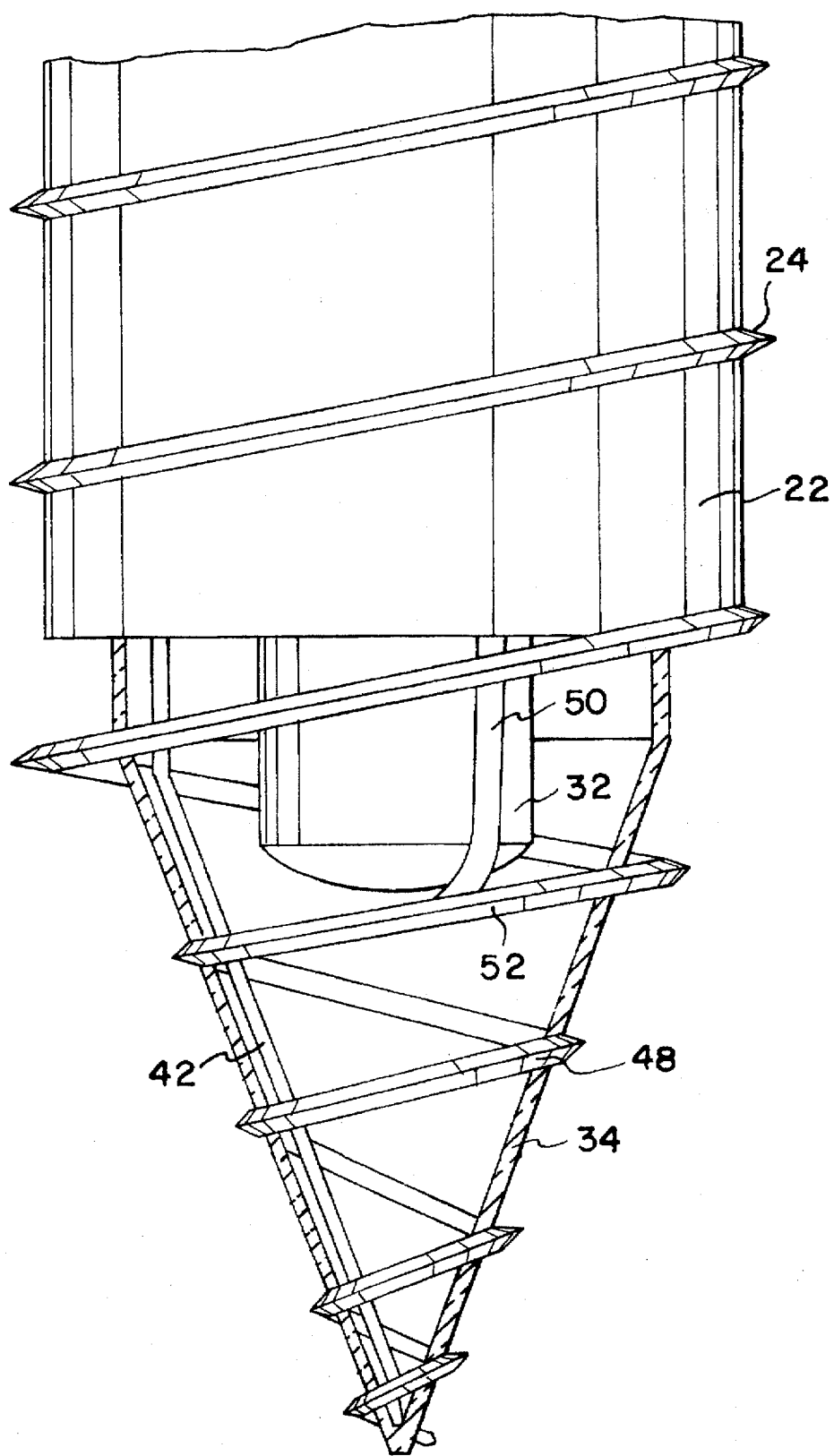
FIG. 7 is a side view of the point of the trocar in an additional embodiment.

In another embodiment shown in FIG. 7, a gripping element is mounted at the point of the trocar, the said gripping element which has the purpose of firmly holding the body tissue during penetration against the pressure of the trocar point. The body tissue, e.g., peritoneum, cannot thereby avoid the trocar point and cannot be vaulted inwardly into the abdominal cavity.

As FIG. 7 shows, the gripping element consists of a rotatable spiral 48, mounted externally to the conical, beveled, or tapered window 34, the said spiral which, for example, is made from a wire having first and second surfaces converging to a helical line, and is fitted to the conical, beveled, or tapered form of the window 34. The spiral 48 is bent at its posterior end into an axis-parallel connecting piece 50, which is shaped at its end into a ring, which is not visible in the figure and is mounted rotatably in a circumferential groove of the shaft 10 of the trocar. By means of the said ring, the spiral screw 48 is thus mounted rotatably on the conical window 34 and firmly held axially. The thread 24 of the sleeve 22 is brought out through the anterior distal sleeve end and acts as a driver point 52 upon the posterior end of the spiral 48, to carry it along during the rotation of the sleeve 22.

To penetrate the body tissue, e.g., the patient's abdominal wall, the sleeve 22 is caused to rotate, whereby is causes the spiral 48 on the conical, beveled, or tapered window 34 to rotate via the driver point 52. Via the rotating spiral 48 and the attached thereto thread 24, the trocar bores into the tissue like a corkscrew, without the said tissue being able to evade the trocar point. As soon as the tissue is penetrated and the trocar point is, for example, in the abdominal cavity, the trocar together with the spiral 48 is held axially on its point can be withdrawn from the sleeve 22. The sleeve 22 can then be used for the insertion of surgical instruments or the like.

In FIG. 8, there is shown an embodiment of a penetration instrument 54 comprising a rigid linear hollow cylindrical shaft 56 and a point 60. The shaft 56 is internally threaded as shown at 58, and the point 60 has a threaded extension 62 for engagement with the threads 58. The shaft 56 and point 60 may be joined in a manner other than that shown, and may be made of a single piece of material. The point 60 is hollow and on the exterior has a cylindrical portion 64 which is adjacent the shaft 56, as when the instrument 54 is assembled, and has substantially the same outer diameter as the shaft 56. Opposite the proximal end of point 60 there is a distal end which is shaped to penetrate body tissue, to create an opening therein and to enlarge the opening as the point 60 is advanced by the application of force to the shaft 56. As will be appreciated, the distal end of the point 60 is forward of the proximal end thereof, and forward of the shaft 56. At the distal end thereof, forwardly of the cylindrical portion 64, there are preferably four planar surfaces 66a, 66b, 66c and 66d. These exterior surfaces of point 60 are inclined towards the distal end of point 60, so that point 60 enlarges in transverse extent from the distal end towards the proximal end. Each two adjacent surfaces 66a, 66b, 66c and 66d form a set of surfaces which converges to a linear edge 68a, 68b, 68c, and 68d, as shown in FIG. 11. The linear edges, which incise or cut, preferably are coplanar with the axis of the instrument 54.

Referring now to FIG. 12, there is shown the point 60 and the surfaces 66b and 66c. The point 60 is opaque, and has an opening through the surfaces 66b and 66c at the distal end thereof; in these openings, there is a transparent window 70, although two separate window elements may be provided. The window 70 may comprise a single or two plastic elements, and may have an external curvature to provide a lens. The point 60 is imperforate, the window 70 closing the opening(s) therein.

Optical elements may be provided within the instrument 54 to emit light to be passed through the window 70, the light being reflected from tissue, organ, etc., and passing through the window 70 and providing an image which is viewed by an optical viewing system. The optical viewing systems may comprise, for example, separate optical fibers, or as shown in FIG. 12, may comprise a fiber-optic bundle 72 containing both light transmitting and light receiving optical fibers; also relay lenses may be used instead of optical fibers.

Referring now to FIG. 13, a further embodiment of an instrument in accordance with the invention is shown, the penetration instrument 74 comprising a linearly extending hollow rigid shaft 76 of circular configuration, and having a threaded extension 78. The point 80 is imperforate, of transparent material, and has internal threads 82 and has a cylindrical portion 84 at its proximal end of the same diameter as the shaft 76. Forwardly of the cylindrical portion 84, the point 80 preferably has a right circular conical distal end portion 86 which converges towards the distal end 90 thereof, which is truncated, and is preferably perpendicular to the axis of end portion 86 as shown, but could be at a different angle, with some reduction in the image acquired.

As shown in FIG. 14, the distal end portion 86 has surfaces converging to linear edges, which are provided by a pair of thin blade members 88a and 88b having the bases thereof embedded in the conical distal end portion 86. The forward or distal ends of the blade members 88a and 88b terminate in a plane which passes through the truncated distal end 90 of in the conical portion 86 of point 80.

As shown in the embodiment of FIG. 15, in the conical terminal portion 86a of point 80a has thin blade members 88c and 88d; the forward or distal ends of these members are rearwardly of the truncated distal end 90a of the conical portion 86a. Consequently, it will be seen that in the embodiments of FIGS. 14 and 15, the thin blade members are at or rearwardly of the distal end 90, 902 of the point 80, 802 so as to enable the surgeon to see tissue or organ prior to the moving of the instrument in a manner to penetrate or cut the tissue or organ. Hence, the surgeon is enabled to view the tissue or organ in advance of the instrument prior to effecting penetration or cutting thereof.

FIG. 16 and FIG. 17 are other views of the point 80, and as will be seen therein, the blade members 88a and 88b are coplanar with the axis of the point 80, and with the axis of the shaft 76.

Referring now to FIG. 18, there is shown the point 80, including the conical portion 86, with the blade elements 88a and 88b having the bases thereof embedded in the conical portion 86. The truncated distal end 90 of the conical portion 86 is also shown, which together with the material of the point 80 which is behind it, functions as a window lying on the axis of the point 80, for viewing of tissue or organ directly ahead of the point 80. As is apparent from FIG. 18, the blade members 88a and 88b have their forward or distal ends substantially in the plane of the truncated planar distal end 90. The distal end of conical portion 86 may terminate in a conical apex; blade members are at or rearwardly of it.

In FIG. 19, there is shown the truncated end 90, the conical portion 86, and the blade elements 88a and 88b; these blade elements contain converging surfaces 88e and 88f, which meet or join at a linear edge 88g, which is the cutting edge of the blade element 88a, 88b.

Referring now to FIGS. 20a, 20b and 20c, the instrument 74 will be seen in successive stages of penetration of a tissue or organ. Initially, there will be obtained a view of the upper surface of the body to be penetrated before penetration begins. As penetration proceeds, as shown in FIGS. 20b and 20c, the tissue or organ is cut or severed, and the surgeon will be able to view an image of the portion of the body being penetrated, through utilization of optical lighting and viewing systems (not shown), and will be able to view tissue or organ adjoining the surface of the conical portion 86. Thus, when the instrument 74 enters into each separate layer of tissue or different element of the body, a view thereof will be obtained prior to the actual penetration or cutting of that layer or element.

The utilization of a penetrating point, of tapering, preferably conical configuration, together with linear edges, which cut tissue or organ, enables the instrument to penetrate tissue or organs with minimal, readily controlled force. For example, with the embodiments of FIGS. 13-19, in which the distal end is planar and truncated, there is only required a force of about 4-8 lb to advance the instrument.

The claims and specification describe the invention presented, and the terms that are employed in the claims draw their meaning from the use of such terms in the specification. Some terms employed in the prior art may be broader in meaning than specifically employed herein. Whenever there is a question between the broader definition of such term as used in the prior art and the more specific use of the term herein, the more specific meaning is meant.

We claim:

1. An instrument for the direct penetration of body tissue comprising:
a point having a proximal end and a distal end, said point having an axis between said proximal and distal ends, and enlarging in transverse extent from the distal end thereof towards the proximal end thereof, whereby said point is shaped to penetrate body tissue to create an opening therein and to enlarge the opening as the point is advanced with the said distal end forward of said proximal end,
said distal end being substantially planar and substantially transverse to said axis, and at least said distal end being a transparent window to enable the transmission of light and the image of tissue, organ and the like,
said point having an element with at least one set of surfaces converging to a linear edge extending from or adjoining the distal end of said point towards the proximal end thereof, said element having a distal end not beyond the distal end of said point,
a rigid linear element at the proximal end of said point for advancing said point into and withdrawing said point from body tissue,
whereby body tissue exteriorly of said point may be viewed prior to cutting and penetration thereof.

2. The instrument of claim 1, said linear edge being coplanar with said axis.

3. The instrument of claim 1, said surfaces of said element being planar.

4. The instrument of claim 3, said point having at least two said elements each with a set of said planar surfaces, each two of said planar surfaces converging to a said linear edge.

5. The instrument of claim 4, said rigid linear element being substantially cylindrical, and said point being substantially cylindrical adjacent said linear element.

6. The instrument of claim 1, said rigid linear element being hollow substantially along the entire length thereof for receiving therein light transmitting and optical viewing systems.

7. The instrument of claim 1, said element being a thin blade.

8. The instrument of claim 7, said thin blade element having a base portion opposite said linear edge, said base portion being embedded in said point.

9. The instrument of claim 1, said point having an axis, said linear edge being substantially coplanar with said axis.

10. The instrument of claim 1, said point being transparent.

11. An optical penetrator for body tissue comprising:
a rigid elongated shaft,
a penetrating point on said shaft having a distal end remote from said shaft and a tapered distal end portion adjacent said distal end increasing in transverse dimension therefrom, said distal end of said penetrating point being a transverse planar distal end, at least said distal end of said penetrating point being transparent,
said penetrating point having at least one set of surfaces converging to a linear edge having one part thereof closer to said distal end of said penetrating point than another part thereof and not extending substantially beyond said distal end of said penetrating point.

12. The optical penetrator of claim 11, said penetrating point having an axis, said planar distal end being transverse to said axis.

13. The optical penetrator of claim 12, said planar distal end being substantially perpendicular to said axis.

14. The optical penetrator of claim 11, wherein said at least one set of surface and said linear edge are portions of a blade member extending outwardly from said tapered distal end portion of said penetrating point.

15. The optical penetrator of claim 14, wherein said linear edge of said blade member is straight, said distal end portion having a surface and said linear edge being substantially parallel to the surface of said tapered distal end portion.

16. The optical penetrator of claim 14, said optical penetrator comprising at least two said blade members, said blade members being circumferentially spaced.

17. The optical penetrator of claim 16, said linear edges being substantially straight.

18. The optical penetrator of claim 17, wherein said linear edges are substantially parallel to said tapered distal end portion.

19. The optical penetrator of claim 11, said linear edge being substantially straight.

20. The optical penetrator of claim 19, said penetrating point being transparent.

21. The optical penetrator of claim 11, said penetrating point being transparent.

22. The optical penetrator of claim 11, said tapered distal end portion of said penetrating point being generally conical, said linear edge extending from outwardly of a part of said conical end portion having a greater transverse dimension to outwardly of a part of said tapered end portion having a lesser transverse dimension, said edge being substantially straight.

23. The optical penetrator of claim 22, said line being substantially parallel to the surface of the generally conical distal end portion.

24. For use with a hollow rigid shaft adapted to receive light transmitting and image transmitting systems,
- a penetrating point of generally conical truncated configuration, said penetrating point having a planar truncated distal end, said planar distal end being transparent, and
- a blade member comprising a set of surfaces converging to a linear edge fixedly secured to and extending outwardly of and along said penetrating point, the linear edge having an end adjacent and not beyond said truncated planar distal end.

25. The structure of claim 24, said penetrating point being transparent.

26. The structure of claim 24, said blade member having a portion thereof opposite said linear edge embedded in said penetrating point.

27. The structure of claim 26, said penetrating point having an axis and said blade member being substantially coplanar with said axis.

28. The structure of claim 24, said penetrating point having an axis and said planar truncated distal end surface being substantially perpendicular thereto.

29. The structure of claim 24, and in combination therewith, a hollow rigid shaft, said penetrating point being at an end thereof.

30. The structure of claim 29, and light and optical viewing systems in said hollow shaft.

31. A surgical penetration device comprising:
- a) an elongated, tubular or sleeve-like member having a space therein and having a first end;
- b) an imaging member, capable of transmitting images received back from the surgical site in advance of and laterally of said device, positioned at or cooperable with said first end, said imaging member comprising a penetrating point having a planar transverse and transparent distal end;
- c) a cutting element positioned on or cooperable with said imaging member to enable said imaging member to pierce and cut tissue, said cutting element not extending beyond said imaging member;
- d) said space in said elongated member being capable of containing a lighting means and a light image receiving means to cooperate with said imaging member.

* * * * *